United States Patent [19]

Yaroshuk et al.

[11] 4,253,768
[45] Mar. 3, 1981

[54] PROCESSING SYSTEM FOR DETECTION AND THE CLASSIFICATION OF FLAWS ON METALLIC SURFACES

[75] Inventors: Nicholas Yaroshuk, White Oak; Miklos Sarkozi, Murrysville; Robert C. Miller, Penn Hills; Paul G. Kennedy, Monroeville, all of Pa.

[73] Assignee: Westinghouse Electric Corp., Pittsburgh, Pa.

[21] Appl. No.: 932,235

[22] Filed: Aug. 9, 1978

[51] Int. Cl.² ............................................. G01N 21/32
[52] U.S. Cl. .................................... 356/431; 250/563; 356/237
[58] Field of Search ............... 356/51, 237, 430, 431, 356/445; 250/563, 572

[56] References Cited

U.S. PATENT DOCUMENTS

| | | | |
|---|---|---|---|
| 2,975,293 | 2/1955 | Kruse, Jr. et al. | 250/219 |
| 3,749,496 | 7/1973 | Heitanen et al. | 356/73 |
| 3,781,117 | 12/1973 | Laycak et al. | 356/200 |
| 3,781,531 | 12/1973 | Baker | 235/151.3 |
| 3,804,534 | 4/1974 | Clarke | 356/237 |
| 3,812,373 | 5/1974 | Hosoe et al. | 250/562 |
| 3,834,822 | 9/1974 | Stapleton et al. | 356/431 |
| 3,843,890 | 10/1974 | Anthony, Jr. et al. | 250/563 |
| 3,900,265 | 8/1975 | Merlen et al. | 356/200 |
| 3,920,970 | 11/1975 | Slaker | 235/151.3 |
| 3,984,189 | 10/1976 | Seki et al. | 356/73 |

Primary Examiner—John K. Corbin
Assistant Examiner—Bruce Y. Arnold
Attorney, Agent, or Firm—R. A. Stoltz

[57] ABSTRACT

This invention is a system of automatically classifying defects both for sorting defective products (metallic surfaces, especially tube surfaces) as to the reworking operation required for correcting the defect, and for classifying the defect as to the preceding manufacturing operation which is the most probable cause of that defect and sending a signal to that operation to provide for adjustments to minimize future defects. The system uses a source of electromagnetic radiation (typically a laser beam which is scanned across the surface) and at least two sensors (adjusted such that the radiation is reflected from a defect-free surface principally received by one of the sensors but that there is a measured amount of radiation in the other sensor). An average signal of the principal sensor is developed as a function of scan position. Threshold circuitry detects when the ratio of sensor signal to average signal varies by a predetermined amount. Special circuitry is used to detect the essentially simultaneous occurrence of at least two different preselected combinations of signal variations to identify the type of defect.

10 Claims, 3 Drawing Figures

PROCESSING SYSTEM FOR DETECTION AND THE CLASSIFICATION OF FLAWS ON METALLIC SURFACES

CROSS-REFERENCE TO RELATED APPLICATION

In concurrently filed application Ser. No. 932,234 filed Aug. 9, 1978, assigned to the same assignee, is described a method for scanning for flaws on a metallic surface utilizing dynamic correction. Individual scan signals are divided into a large number of increments, each increment representing a predetermined position in the scan. A dynamic average is computed for each of the scan positions and flaws are detected by comparing the increment signals to the dynamic average signal for the same position. Such a technique is especially useful to detect flaws in high-quality tubing, such as used for nuclear reactor fuel rods or for nuclear reactor steam generator tubing. The technique of the related application and the system of this application can be used together for automated inspection.

BACKGROUND OF THE INVENTION

This invention relates to a technique for detecting flaws on surfaces, and, more particularly, to automatically analyze signals from a surface examining system.

Before the development of this technique, tubing inspection on nuclear reactor steam generator tubing and the Zircaloy nuclear reactor fuel rods was performed and analyzed manually. Such visual flaw/defect inspection tasks are dependent upon human operation and interpretation. This method lacks a definitive and accurate reference, lacks consistency, is slow and tedious, and adds significantly to product cost. Where ultra-high reliability is required, however, none of the prior art automatic scanning systems were able to locate and classify defects as effectively as the human inspectors.

A large number of surface scanning systems have been proposed in the past. U.S. Pat. No. 2,975,293 issued to Kruse et al. on Mar. 14, 1961 and U.S. Pat. No. 3,804,534, issued to Clarke on Apr. 16, 1974 illustrate such scanning systems. The use of more than one detector for rough surfaces is taught, for example, in U.S. Pat. No. 3,984,189 issued to Seki et al. Generally, the prior art scanning systems were designed for flat surfaces, but U.S. Pat. No. 3,749,496 issued to Hietanen et al. on July 31, 1973 illustrates the inspection of the inside surface of a cylindrical workpiece. Generally such inspection devices are stationary and the surface is moved.

Some systems have used electronic logic or memories for defect evaluation including means to prevent indications of multiple flaws when a single flaw is scanned by consecutive scans. See, for example, the following U.S. Pat. Nos.: 3,900,265 issued to Merlen et al. on Aug. 19, 1975; 3,812,373 issued to Hosoe et al. on May 21, 1974; and 3,781,117 issued to Laycak et al. on Dec. 25, 1973. Some systems use averaging of the signal from the preceding portion of the scan (passing the scan signal through a low pass filter) to develop a base line signal, and then compare the instantaneous signal to the base line signal in order to partially compensate for the gradual variations in sensitivity throughout a scan. U.S. Pat. Nos. 3,781,531 issued to Baker on Dec. 25, 1973 and 3,920,970 issued to Slaker on Nov. 18, 1975 illustrate this technique. The sensitivity of such circuits is limited as the error threshold must be set away from the base line not only by the normal amount of noise, but also by the amount which the base line shifts during the filtering period.

While the prior art methods have been satisfactory for some applications, higher quality products, such as nuclear reactor fuel tubing and nuclear reactor steam generator tubing have required closer inspection. As a result, slow manual inspection methods have been heretofore used for such products.

SUMMARY OF THE INVENTION

This invention provides for automated detection and classification of defects in metallic surfaces which have been subject to at least two manufacturing steps. Generally, the surface is advanced past a source of electromagnetic radiation which is directed toward the surface. The radiation reflected from the surface is sensed by an electromagnetic radiation sensing means using at least two sensors. Scanning is provided by moving the source or the sensor (or both) generally transverse to the direction in which the surface is advanced, producing a series of serial (multiple areas of the surface are not scanned in parallel; at at any given time, the signal represents a single small area) scan signals. The effective relative position of the source and the sensors are adjusted such that an essentially defect-free surface reflects radiation principally to the first sensor but reflects a measured amount of radiation to a second sensor. An average signal of the first sensor as a function of position is generated by circuitry, for example, as described in the aforementioned related application. The first sensor signal is compared to the average signal (all signals are compared to the average for the same scan position and a first type of error-indication signal is generated if this first sensor signal exceeds the average signal by a predetermined amount (e.g. 20% greater than the average signal). A second type of error indication is generated if the first sensor signal (Y signal) is less than the average signal by another predetermined amount (e.g., the Y signal is less than 60% of the average signal). At least one additional radiation sensor is used and its signal is also compared to the average signal. A third error signal is generated when this additional signal exceeds a predetermined fraction of the average signal (e.g. 45%) and a fourth error signal is generated when this additional signal exceeds a second predetermined fraction of the average signal (e.g., 60%). Simultaneous occurrence of preselected conditions of error signals are used to provide defect classification signals, and these classification signals are used to indicate rejection of the surface and the type of defect which occurred. These defect classification signals are also used to feed an indication of the type of defect which has occurred back to the preceding manufacturing steps such that process control can be implemented on the manufacturing step which is the most likely cause of that type of defect, thus minimizing the future occurrences of the defect.

BRIEF DESCRIPTION OF THE DRAWINGS

A better understanding of the invention may be had by reference to the drawings, in which.

DESCRIPTION OF THE PREFERRED EMBODIMENTS

Figure 1:
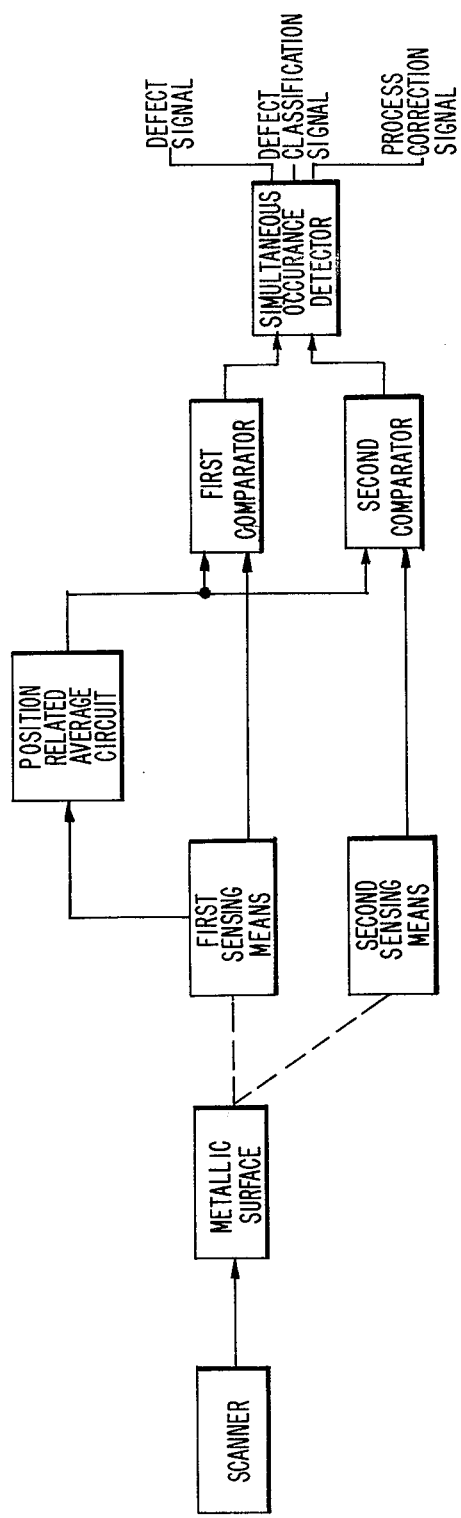
FIG. 1 is a block diagram showing the relationship between elements of the system.

The scanner and sensing means of FIG. 1 can be any of a variety of configurations which provide a serial signal with time (not parallel signals from different positions at one time) of the type given by a sensor repeatedly moved across a surface. The scanning is generally provided by moving (scanning) the spot of radiation directed across the surface to be inspected, but could be provided by a source of radiation covering the entire line to be scanned and moving the sensor of the reflected radiation, or even by having a constant line of radiation impinging on the surface and having a large number of sensors which are electronically scanned to produce the same type of serial output signal as the other techniques. In any case the amplitude of the serial output signal is to be a function of the radiation reflected from the surface, and the timing within the scan is to be related to position within the scan. At any one point in time, the signal (or signals) represent reflection from a single small spot on the surface.

The preferred embodiment of this invention is with a stationary laser whose beam is passed through an acoustical scanner to cause the laser beam to be repeatedly scanned across the surface. The sensors are also stationary and the surface is moved past the system such that the line scanned by the laser beam will inspect the surface area. Although two sensors could be used, three sensors are preferred to provide a more straightforward optical system. The system is adjusted so that most of the energy is reflected to the center sensor system (when the spot on the surface being scanned is defect-free). Defects such as dents or scratches will deflect more light to at least one of the outside sensors while other defects (such as stains or pits) will lower the radiation received by the center channel without increasing the radiation received by either of the outside sensors.

The compensation circuitry preferably produces dynamic averages on an increment (small scan segment) by increment basis. Thus, if a particular increment of the scan remains low, scan after scan, because of a non-linearity in the optical scanner for example, the dynamic average in that portion of the scan will be low and will compensate for the nonlinearity.

Vibration can be especially troublesome during inspection of tubing. Dynamic averaging compensates for vibration if the averaging is over a comparatively short period. Averaging over about 16 scans with 5300 scans per second has proven satisfactory for tube inspection.

Figure 2:
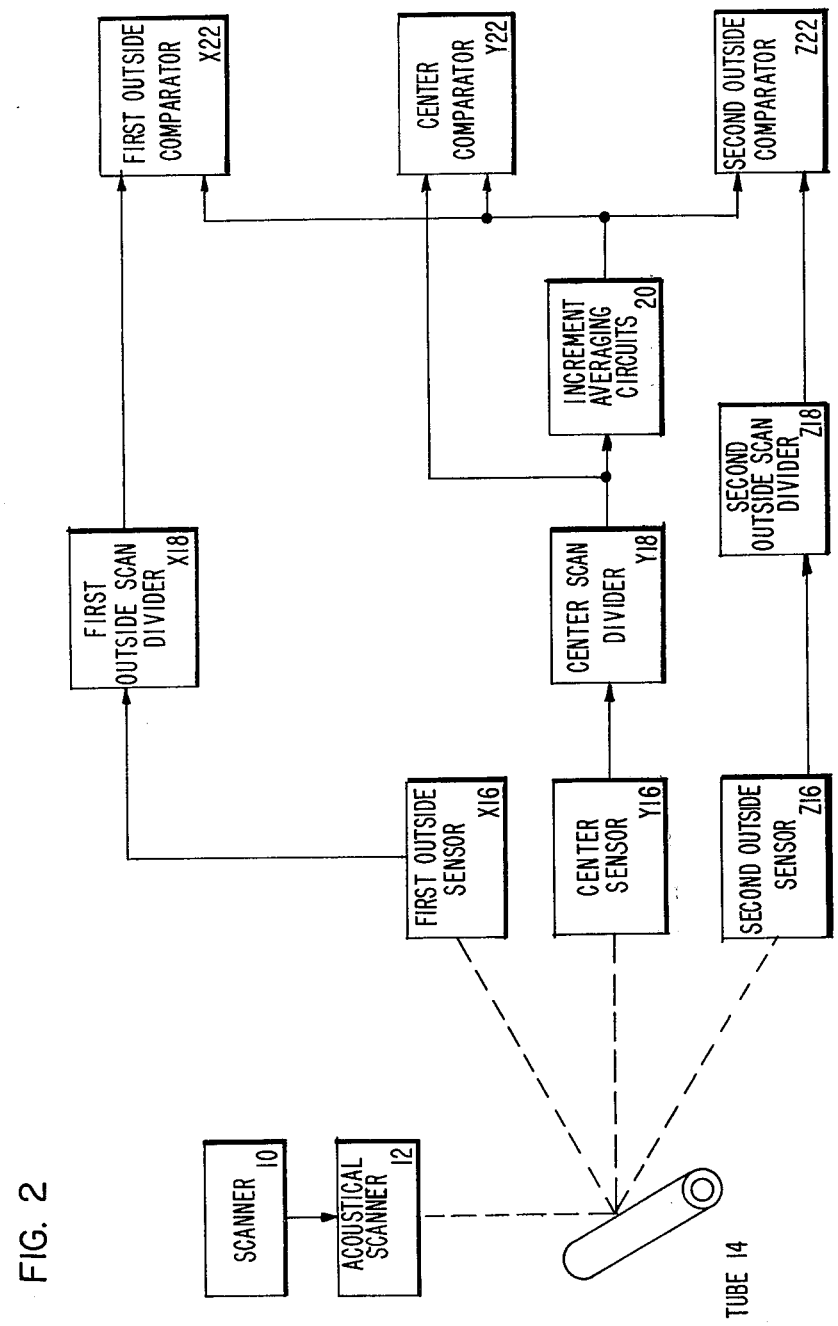
FIG. 2 is a block diagram showing a three sensor arrangement.

The block diagram in FIG. 2 shows a three-sensor arrangement in which the average of the center sensor is used as a basis for comparison for all three sensor signals. In this configuration a laser beam is repeatedly scanned across the surface of the tube by an acoustical scanner. The tube is simultaneously fed axially and rotated such that the scanning lines cover the entire surface of the tube (during one rotation the tube is fed axially just less than the length of the scan so that there is a small amount of overlap). The system is adjusted (with no defect on the tube) so that most of the light is reflected to the center sensor but that a detectable amount of light is reflected to outside sensors.

In this particular system each scan is divided into 128 increments. Each of the 128 average values are updated each cycle (a separate average value for each of these 128 scan increments). Thus, at the time the laser beam is in a position approximately half way through the scan (on the 64th increment, for example) three 64th increment values will be sensed (one for each of the outside channels and one for the center channel). All three of these 64th increment values will be compared to the average value (of the center sensor) for the 64th increment.

Figure 3:
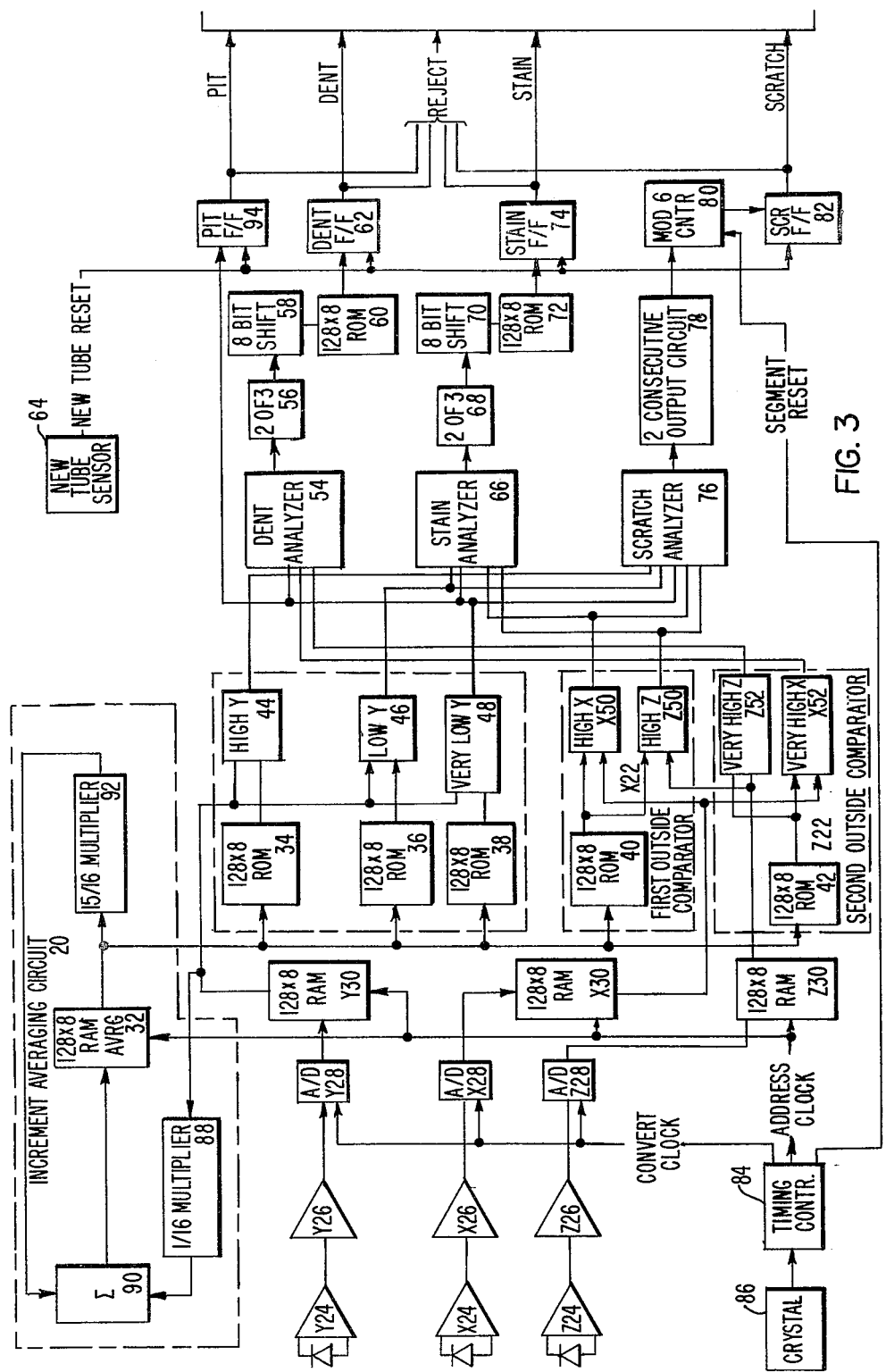
FIG. 3 is a diagram showing details of the surface analysis circuitry.

FIG. 3 shows details of a particular embodiment. These analyses can be done with two detectors (rather than three as described below) merely by omitting the "Z" signals, but a three-detector system is preferred. In this embodiment the analog signal from the three sensors (here silicon photodiodes) are run through amplifiers to A-to-D converters to produce 128 digital values per sensor per scan. These three sets of 128 digital values are stored in order in three random access memories. In this embodiment, there is a scan portion of the cycle, during which the laser beam scans the tube and the sensor values are digitized and stored, and there is an analyzing portion of the cycle (here using the same length of time as the scan portion) in which the data in each scan increment in the X, Y and Z random access memories ($X_i$, $Y_i$ and $Z_i$) is compared to the average value in the Y channel for that incremental position in the scan. When any comparison of the X, Y and Z signals falls outside certain predetermined limits, an error signal is generated (in most cases, multiple error indications are necessary to cause a reject).

In particular, light (from a laser beam, scanned by an acoustic scanner, and reflected off the tube surface as in FIG. 2) is picked up by silicon photo diodes X16, Y16 and Z16. The electrical signal is amplified by X24, Y24, Z24 and further amplified by X26, Y26, and Z26. During the scan portion of the cycle, the convert clock pulse causes each of the A-to-D converters X28, Y28 and Z28 to generate 128, 8-bit incremental signals (each of the incremental values being represented by 8 binary bits). These incremental signals are then stored in order by position within the scan in 128 by 8 random access memories X30, Y30 and Z30.

After the scan portion is complete, the analyze portion begins. The address clock addresses the first memory position (the first scan increment) in the random access memories X30, Y30 and Z30 and also the first position in the increment average random access memory 32. The average value for this first increment ($\overline{Y_i}$) is then multiplied by predetermined constants using read only memories 34, 36, 38, 40 and 42 (here, read only memories are used in a table lookup fashion to provide multiplication by the predetermined constant) to provide threshold values for comparison. The latest values for X, Y and Z for the first incremental position ($X_i$, $Y_i$ and $Z_i$) are compared to the threshold values in comparators 44, 46, 48, 50, 52, 54 and 56 to provide indication of when any of the signals have deviated from their normal relationship to the center sensor average for that first increment. Thus, for example multiplier 34 gives an effective multiplication of about 1.2 and comparator 44 will provide an output when the value of $Y_i$ exceeds 1.2 times the corresponding increment average of $\overline{Y_i}$. Similarly, multiplier 36 provides a constant such that comparator 46 gives an output when $Y_i$ is less than 60 percent of $\overline{Y_i}$. Similarly, multiplier 38 and comparator 48 gives an output on a very low values of Y (when $Y_i$ is less than 0.5 times $\overline{Y_i}$). Multiplier 40 and comparators X50 and Z50 provide an output when the latest X or Z values ($X_i$ or $Z_i$) rise above about 45 percent of $\overline{Y_i}$.

Multiplier 42 and comparators X52 and Z52 provide outputs when either $X_i$ or $Z_i$ rise above 60 percent of $\overline{Y}_i$.

The logic circuitry not only indicates rejects, but also classifies the defects. This allows for sorting the tubes for subsequent analysis and repair, and also for signalling the appropriate preceding work stations such that process alterations may be made which will minimize the number of defects. It has been found convenient to classify the defects as "pits," "dents," "stains," or "scratches." "Dent" analyzer 54 is activated by a very low Y ($Y_i^{--}$) signal from comparator 48, together with a very high X ($X_i^{++}$) or Z ($Z_i^{++}$) signal from comparators Z52 or X52. Two error indications out of three consecutive increments will provide an output from the dent two-out-of-three circuit 56. Filtering circuits such as circuit 56 provide smoothing to minimize erroneous error signals (e.g., those generated by electrical noise). The output from the two-out-of-three circuit 56 is further filtered by an 8-bit shift register 58 and pattern analysis circuit 60 (here a 128×1 read only memory). This arrangement of shift register plus read only memory is used to indicate two consecutive outputs of the two-out-of-three circuit 56. When the "dent" criteria is met, the "dent" flip-flop 62 is set, the tube is marked for rejection and segregation to a reject hopper. The "dent" rejection signal is maintained until reset by the new tube sensor 64. The "dent" analyzer circuit 54 is activated by the $Y_i$ very low signal from comparator 48 simultaneously with either the $X_i$ or $Z_i$ very high signal from comparators X52 or Z52 ($X_i$ alone would be used rather than "$X_i$ or $Z_i$" if only two detectors were used).

The "stain" analyzer 66 includes a two-out-of-three circuit 68, shift register 70, read only memory 72, and "stain" flip-flop 74. It operates in a similar manner to the previously described "dent" circuit except that the criteria for an output of the "stain" analyzer 66 is a low Y ($Y_i^{-}$) indication from comparator 46, but not a very low Y ($Y_i^{--}$) indication from comparator 48 and also neither a high $X_i$ nor high $Z_i$ indication from comparators X50 or Z50. Thus, the control condition is: $Y_i^{-}$ and not $Y_i^{--}$ and not $X_1^{+}$ and not $Z_i^{+}$ ($Y_i^{-}$ and not $Y_i^{--}$ and not $X_i^{+}$, would be the condition if only two detectors were used).

The "scratch" analyzer circuit gives an output with low $Y_i$ from comparator 46 but not very low $Y_i$ from comparator 48. High $X_i$ from comparator X50 or high $Z_i$ from comparator Z50 but not high $Y_i$ from comparator 44 is also interpreted as a "scratch." Thus, the control condition is either: ($Y_i^{-}$ and not $Y_i^{--}$) or (($X_i^{+}$ or $Z_i^{+}$) and not $Y_i^{+}$). If only two detectors were used, the control condition would, of course, be ($Y_i^{-}$ and not $Y_i^{--}$) or ($X_i^{+}$ and not $Y_i^{+}$). The output of analyzer 76 goes into a filtering arrangement consisting first of the two-consecutive-output circuit 78 and then the counter 80. Counter 80 is reset by the segment reset every 32 scans. If the counter 80 gets to 6 before being reset, it sets the "scratch" flip-flop 82 and marks the tube to be rejected. The segment reset, like the convert clock (during the scan portion of the cycle) and the address clock (during the analyze portion of the cycle) is generated by the timing and control circuit 84 which, in turn, is driven by the 20 MHz crystal oscillator 86.

The analysis circuit for "dents," "stains" and "scratches," as described above, uses special or shift register and read only memory combinations 58 and 60, 70 and 72 to provide filtering to avoid rejection from electrical noise or on minor surface blemishes. The "pit" detection circuitry, however, has no such filtering as even a very small pit could represent a serious defect. The Y very low ($Y_i^{--}$) indication from comparator 48 is an indicator of a pit and this output is fed directly to the "pit" flip-flop 94. Thus, a single incident of output from the $Y_i^{--}$ comparator 48 will cause rejection of the tube.

The average for each increment of the scan ($\overline{Y}_i$) is calculated during the analysis cycle at the same time the $X_i$, $Y_i$, and $Z_i$ values are analyzed. As each increment is addressed by the address clock, the output of the random access memory Y30 is fed through a times 1/16 multiplier 88 and then to a summing circuit 90. The $\overline{Y}_i$ calculated on the previous cycle is fed from the averaging random access memory 32 through a times 15/16 multiplier 92 (at the same time, the $\overline{Y}_i$ value is also being fed to multipliers 34, 36, 38, 40 and 42 for comparison to $X_i$, $Y_i$ and $Z_i$). The output of the 15/16 multiplier 92 is fed to the summing circuit 90 where it is combined with the output of multiplier 88 (1/16 the latest value of $Y_i$) and this updated value of $\overline{Y}_i$ is then stored back in the averaging random access memory 32. This process is repeated to calculate a new $\overline{Y}_i$ value for each of the 128 increments during each analysis period.

While the above description has used one channel which receives the principal amount of radiation from a defect-free surface (the Y sensor) and two additional sensors, both of which receive a small, but measureable, amount of radiation from a defect-free surface (the X and Z sensors), optical systems can be used which effectively combine the light which would be received by either of the X or Z sensors and thereby accomplish the analysis with only two sensors. Similarly, combinations with one principal sensor and more than two additional strategically placed sensors can also be used by merely analyzing for the occurrence of high (or very high) indications in any of these additional sensor outputs.

The thresholds for what is to provide an error indication can be varied. Multiplier 34 will always have a multiplication greater than one (1) to indicate the $Y_i$ value is greater than the average value. Similarly, the multiplier 36 for low Y value can be varied from the 0.6 value given above, but in all cases will be less than one, and the predetermined constant for very low value of Y can vary from the 0.5 value given above, but in all cases will be less than the constant for low Y. The constant for high values for X (or X and Z) can vary from the 0.5 value, but in all cases will be less than the very high X (or X and Z) which in turn will always be less than one. While it is convenient to have the high X threshold to be the same as the high Z threshold, the X and Z thresholds for high (or very high) values do not have to be the same.

Although the use of the dynamic averaging circuit described in the above-mentioned related application has clear advantages, other types of arrangements for generating an average signal as a function of scan position could be used. A static correction could be used using measurements made of reflection versus scan position during calibration of the equipment, and using these measurements to adjust the amount of signal such that an essentially constant signal is given throughout the scan for a defect-free surface. This correction can be mechanical (e.g., a method of blocking an appropriate amount of light at the various scan positions to give a constant amount of light at the sensors at all scan positions) or an electronic adjustment (e.g., compensating by varying the gain of the preamplifiers as a function of scan position).

The relationship between type of defect and the cause of that type of defect will vary with various manufacturing processes. It has been found that in the manufacturing of nuclear tubing, that pits are generally caused by the pilgering operation or the pickling operation. Scratches have generally been found to be due to the various testing operations as, for example, the spiral scratches caused by misadjustment of the head of the ultrasonic testing operation. The testing operation for end squareness has been found to be one of the major factors in staining of tubing, especially on stains near the end of the tubing.

The above variations are illustrative of the inventive concept described herein, but the invention should not be construed as limited to the particular form as described, as these described forms are intended to be illustrative rather than restrictive. The invention is intended to cover all forms which do not depart from the spirit and scope of the invention.

What is claimed is:

1. In an automatic surface scanning method of the type in which surfaces have been subjected to at least two manufacturing steps, said method utilizing advancing a surface past a source of electromagnetic radiation, directing said electromagnetic radiation toward said surface, sensing reflected radiation from said surface with electromagnetic-radiation sensing means, and effectively scanning at least one of said source and said radiation sensing means across said surface generally transverse to the direction in which said surface is advanced to produce a series of serial scan signals, an improvement utilizing defect classification, said improvement comprising:
   a. using a first radiation sensor and a second sensor, each sensor generating a signal which is a function of the amount of radiation received;
   b. adjusting the relative position of said radiation source and said sensors so that an essentially defect-free surface reflects radiation principally to said first sensor and reflects a measured amount of radiation to said second sensor;
   c. generating a first sensor, position-related, average signal;
   d. comparing said first sensor signal to said average signal and generating a first error signal if said first sensor signal exceeds said average signal by a first predetermined amount, and generating a second error signal if said first sensor signal is less than said average signal by a second predetermined amount;
   e. comparing said second radiation sensor signal to said first sensor average signal and generating a third error signal when said second signal exceeds a first predetermined fraction of said average signal and generating a fourth error signal when said second signal exceeds a second predetermined fraction of said average signal, both said first and said second predetermined fractions being greater than the ratio of said measured amount of radiation received by said second sensor from said essentially defect-free surface to said first sensor average signal and both said fractions being less than one, and said second predetermined fraction being larger than said first predetermined fraction;
   f. detecting the essentially simultaneous occurrence of at least two preselected conditions involving at least two of said error signals to provide defect classification signals;
   g. utilizing said classification signals to indicate rejection of said surface and to indicate the defect classification; and
   h. utilizing at least one of said classification signals to indicate to at least one of said at least two manufacturing steps that there has been an occurrence of a classification defect, whereby process control can be implemented to minimize the future occurrences of said classification defect.

2. The method of claim 1 wherein there are at least two types of said classification signals each of which is utilized to indicate to at least one of said at least two manufacturing steps that there has been an occurrence of a given type of classification defect.

3. The method of claim 2, wherein said first sensor signal is compared to said average signal and a fifth error signal is generated if said first sensor signal is less than said average signal by a third predetermined fraction, said third predetermined fraction being greater than said second predetermined fraction, whereby surfaces may be rejected upon very low values of said first sensor signal.

4. The method of claim 2, wherein defect classification signals are utilized to sort said rejected surfaces into defect classifications, whereby reworking and grading of said surfaces may be efficiently implemented.

5. The method of claim 3, wherein a first condition of error signals is used, said condition comprising the essentially simultaneous occurrence of said fifth error and said fourth error signals, whereby a dent is indicated.

6. The method of claim 5, wherein a second condition of error signals is used, said second condition comprising the essentially simultaneous occurrence of said second error signal without the occurrence of either said fifth or said third error signal, whereby a stain is indicated.

7. The method of claim 3, wherein a third condition of error signals is utilized to provide a third defect classification signal, said third condition of error signals comprising either: the essentially simultaneous occurrence of said second error signal without the occurrence of said fifth error signal; or the essentially simultaneous occurrence of said third error signal without the occurrence of said first error signal, whereby a scratch is indicated.

8. The method of claim 3, wherein a third sensor is used to generate a signal which is a function of the amount of radiation received by said third sensor and which third sensor is adjusted to receive a measured amount of radiation from an essentially defect-free surface; a sixth error signal is generated when said third sensor signal exceeds said first predetermined fraction of said average signal; a seventh error signal is generated when said third sensor signal exceeds said second predetermined fraction of said average signal; and a fourth condition of error signals is used, said fourth condition of error signals comprising the essentially simultaneous occurrence of said fifth error signal with at least one of said fourth and seventh error signals, whereby a dent is indicated.

9. The method of claim 8, wherein a fifth condition of error signals is used, said fifth condition comprising the essentially simultaneous occurrence of said second error signal without the occurrence of any of said fifth, third or sixth error signals, whereby a stain is indicated.

10. The method of claim 9, wherein a sixth condition of error signals is used, said sixth condition comprising either: the essentially simultaneous occurrence of said second signal without the occurrence of said fifth error signal; or the essentially simultaneous occurrence of at least one of said third and said sixth error signals without the occurrence of said first error signal, whereby a scratch is indicated.

* * * * *